US009764067B2

(12) United States Patent
Fleury et al.

(10) Patent No.: US 9,764,067 B2
(45) Date of Patent: Sep. 19, 2017

(54) SUPERHYDROPHOBIC COATING FOR AIRWAY MUCUS PLUGGING PREVENTION

(71) Applicant: Boston Scientific Scimed, Inc., Maple Grove, MN (US)

(72) Inventors: Sean P. Fleury, Brighton, MA (US); Mark D. Wood, Shrewsbury, MA (US); Dane T. Seddon, Boston, MA (US); Laura Elizabeth Firstenberg, Worcester, MA (US); Paul Smith, Smithfield, RI (US); Gary J. Leanna, Holden, MA (US); Claude O. Clerc, Marlborough, MA (US); James Weldon, Newton, MA (US); Steven E. Walak, Natick, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 167 days.

(21) Appl. No.: 14/210,612

(22) Filed: Mar. 14, 2014

(65) Prior Publication Data
US 2014/0277443 A1 Sep. 18, 2014

Related U.S. Application Data

(60) Provisional application No. 61/799,312, filed on Mar. 15, 2013.

(51) Int. Cl.
A61F 2/00 (2006.01)
A61L 31/14 (2006.01)
(Continued)

(52) U.S. Cl.
CPC ............ A61L 31/14 (2013.01); A61F 2/0077 (2013.01); A61F 2/07 (2013.01); A61F 2/82 (2013.01);
(Continued)

(58) Field of Classification Search
None
See application file for complete search history.

(56) References Cited

U.S. PATENT DOCUMENTS 4,655,771 A 4/1987 Wallsten
5,662,713 A 9/1997 Andersen et al.
(Continued)

FOREIGN PATENT DOCUMENTS

WO 2010022107 2/2010
WO 2010033482 3/2010
(Continued)

OTHER PUBLICATIONS

Freitag, "Airway Stents," European Respiratory Monograph, 2010, 48(Interventional Pulmonology): 190-217.
(Continued)

Primary Examiner — Katrina Stransky
Assistant Examiner — Wade P Schutte
(74) Attorney, Agent, or Firm — Seager, Tufte & Wickhem, LLP

(57) ABSTRACT

A method for reducing mucus accumulation in an airway including disposing an implantable device within an airway, wherein the implantable device has a first end, a second end, and an inner surface defining a lumen extending from the first end to the second end; wherein at least a portion of the inner surface has a hydrophobic polymer coating thereon, wherein a polymer coating surface has dynamic water contact angles of 145 degrees or greater; and wherein the implantable device is constructed and arranged to maintain patency of the airway; wherein accumulation of mucus is reduced as compared to a similar implantable device without the hydrophobic portion of the inner surface. An implantable medical device having a superhydrophobic surface and a method of making an implantable medical device having a
(Continued)

superhydrophobic surface are also provided. An implantable medical device having a micropatterned surface with enhanced adhesion to tissue, optionally in combination with other region(s) having a superhydrophobic surface and a method of making such a device. Methods and devices for prevention of bacterial adhesion to implanted medical devices.

20 Claims, 7 Drawing Sheets

(51) Int. Cl.
    *A61F 2/82*    (2013.01)
    *A61L 31/10*   (2006.01)
    *A61F 2/07*    (2013.01)
    *A61F 2/86*    (2013.01)
    *A61F 2/04*    (2013.01)

(52) U.S. Cl.
    CPC .............. *A61L 31/10* (2013.01); *A61F 2/86* (2013.01); *A61F 2002/043* (2013.01); *A61F 2230/0067* (2013.01); *A61F 2230/0091* (2013.01); *A61F 2250/0026* (2013.01); *A61F 2250/0039* (2013.01); *A61F 2250/0051* (2013.01); *A61F 2250/0056* (2013.01); *A61L 2400/12* (2013.01); *A61L 2400/18* (2013.01)

(56) References Cited

U.S. PATENT DOCUMENTS

| | | | |
|---|---|---|---|
| 5,876,448 | A | 3/1999 | Thompson et al. |
| 6,071,273 | A | 6/2000 | Euteneuer et al. |
| 6,254,609 | B1 | 7/2001 | Vrba et al. |
| 6,733,487 | B2 | 5/2004 | Keith et al. |
| 6,755,869 | B2 | 6/2004 | Geitz |
| 7,763,455 | B2 * | 7/2010 | Cima .................. B01L 3/5085 424/449 |
| 8,043,359 | B2 * | 10/2011 | Edin ........................ A61F 2/06 424/426 |
| 9,108,880 | B2 * | 8/2015 | Jin ...................... B81C 1/00206 |
| 2002/0010489 | A1 | 1/2002 | Grayzel et al. |
| 2003/0004535 | A1 | 1/2003 | Musbach et al. |
| 2005/0113936 | A1 * | 5/2005 | Brustad ............ A61B 17/06166 623/23.71 |
| 2006/0240218 | A1 * | 10/2006 | Parce .................... B82Y 30/00 428/98 |
| 2007/0005024 | A1 * | 1/2007 | Weber .................... A61L 29/14 604/265 |
| 2008/0226694 | A1 | 9/2008 | Gelbart et al. |
| 2009/0182303 | A1 | 7/2009 | Walak et al. |
| 2009/0294732 | A1 | 12/2009 | Atanasoska et al. |
| 2012/0035715 | A1 | 2/2012 | Robida et al. |
| 2013/0268063 | A1 | 10/2013 | Firstenberg et al. |
| 2014/0276203 | A1 | 9/2014 | Bertolino et al. |
| 2014/0276407 | A1 | 9/2014 | DeVries et al. |
| 2014/0277395 | A1 | 9/2014 | Firstenberg et al. |

FOREIGN PATENT DOCUMENTS

| | | |
|---|---|---|
| WO | 2012167017 | 12/2012 |
| WO | 2013152338 A1 | 10/2013 |
| WO | 2014143750 A1 | 9/2014 |

OTHER PUBLICATIONS

Quéré, "Surface chemistry: Fakir droplets," Nature Materials, Sep. 2002; 1:14-15.
"Aero® Fully Covered Tracheobronchial Stent," Merit Medical Systems, Inc., South Jordan, UT, 2013, http://endotek.merit.com/products/pulmonary.aspx, last accessed Mar. 13, 2013, 2 pgs.
"Aero® Tracheobronchial Stent Technology System," Merit Medical Systems, Inc., South Jordan, UT, May 15, 2009, 1-16; 8 pgs.
Axisa et al., "Low cost, biocompatible elastic and conformable electronic technologies using MID in stretchable polymer," Conf. Proc. IEEE Eng. Med. Biol. Soc., 2007; 2007:6593-6596.
Desai et al., "Plastic masters-rigid templates for soft lithography," Lab Chip, Jun. 7, 2009;9(11):1631-1637.
Dodou et al., "Mucoadhesive micropatterns for enhanced grip," Conf. Proc. IEEE Eng. Med. Biol. Soc., 2007;2007:1457-1462.
Jeong et al., "Nanohairs and nanotubes: Efficient structural elements for gecko-inspired artificial dry adhesives," Nano Today, Aug. 2009, 4(4):335-346.
Kroetch, "NanoFab's PDMS Microfluidic Device Fabrication Manual," University of Alberta, Alberta, Canada; Sep. 2004, 8 pgs. (available online at http://www.nanofab.ualberta.ca/wp-content/uploads/2009/03/boxedpdms.pdf, last accessed Mar. 10, 2013).
Kwon et al., "Friction enhancement via micro-patterned wet elastomer adhesives on small intestinal surfaces," Biomed. Mater., Dec. 2006;1(4):216-220.
Lotters et al., "The mechanical properties of the rubber elastic polymer polydimethylsiloxane for sensor applications," J. Micromech. Microengineering, 1997, 7(3):145-147.
Mahdavi et al., "A biodegradable and biocompatible gecko-inspired tissue adhesive," Proc. Natl. Acad. Sci. U.S.A., Feb. 19, 2008;105(7):2307-2312.
Majidi, "Enhanced Friction and Adhesion with Biologically Inspired Fiber Arrays," University of California, Berkeley, Ph.D. thesis, May 15, 2007, 143 pgs.
Tooley et al., "Thermal fracture of oxidized polydimethylsiloxane during soft lithography of nanopost arrays," J. Micromech. Microeng., 2011, 21:054013 (9 pgs).

* cited by examiner

SUPERHYDROPHOBIC COATING FOR AIRWAY MUCUS PLUGGING PREVENTION

CROSS REFERENCE TO RELATED APPLICATIONS

This application claims the benefit of provisional U.S. Patent Application Ser. No. 61/799,312 (entitled SUPERHYDROPHOBIC COATING FOR AIRWAY MUCUS PLUGGING PREVENTION, filed on Mar. 15, 2013), which is hereby incorporated by reference in its entirety.

The following patent applications are incorporated herein by reference, each in its entirety:

U.S. Pat. App. Ser. No. 61/798,685 (Firstenberg et al.), entitled ANTI-MIGRATION MICROPATTERNED STENT COATING, filed on Mar. 15, 2013;

U.S. Pat. App. Ser. No. 61/798,897 (Seddon et al.), entitled ANTI-MIGRATORY STENT COATING, filed on Mar. 15, 2013;

U.S. Pat. App. Ser. No. 61/798,794 (Clerc), entitled DELIVERY DEVICE FOR PARTIALLY UNCONSTRAINED ENDOPROSTHESIS, filed on Mar. 15, 2013;

U.S. Pat. App. Ser. No. 61/798,545 (Leanna et al.), entitled MEDICAL DEVICES HAVING MICROPATTERN, filed on Mar. 15, 2013; and U.S. Pat. App. Ser. No. 61/798,991 (Bertolino et al.), entitled BIOPSY TOOL HAVING MICROPATTERN, filed on Mar. 15, 2013.

FIELD

This disclosure relates to a method for reducing mucus accumulation in an airway, an implantable device, and a method of making the implantable device.

BACKGROUND

Implantable devices have been implanted in, for example, airways to treat respiratory diseases. However, accumulation of mucus at the superior and inferior ends of an implantable device (e.g., a stent, an airway stent, etc.) has been a concern. Examples of stents include those disclosed in U.S. Pat. No. 4,655,771 (Wallsten), U.S. Pat. No. 5,662,713 (Andersen et al.), U.S. Pat. No. 5,876,448 (Thompson et al.), and U.S. Pat. Appl. Pub. No. 2012/0035715 (Robida et al.).

Proper mucus secretion is useful for clearing foreign matter from the respiratory system. Mucus may include a mixture of materials including, for example, water and glycoproteins and may be produced by, for example, serous cells, goblet cells, Clara cells, and type II alveolar cells in the bronchials and trachea. Stretching of the cells initiates signaling pathways from the CNS to secrete the mucus while the mechanical forces of the cilia and air flow work to transport the mucus through the airway to be expelled from the body.

Accumulation of mucus in an airway is not desirable. For example, accumulation of mucus may result in an infection or inflammation of tissue near the accumulation. Transport of mucus through an airway is dependent on a number of factors including, but not limited to, the composition and properties of the mucus, the quantity of accumulated mucus, the degree of adherence of the mucus to the walls of the airway, the dimensions and configuration of the airway (e.g., cross-sectional area), and the linear velocity of air flowing through the airway due to breathing, coughing, etc. For a given volumetric flow rate of air, the velocity will be higher at portions of the airway having a smaller cross-sectional area and lower at portions of the airway with a larger cross-sectional area. Airway stents have been designed to have a sufficient amount of radial force to maintain patency in the airway. Thus, reducing the cross sectional area in or near the stent ends (e.g., radial compression of the airway) to help prevent mucus buildup may be counterproductive with respect to the objective of maintaining patency.

Some patients that have respiratory diseases have been given a stent for palliative purposes. The presence of a rigid prosthesis may, in some circumstances, have a detrimental effect on the airway's ability to expel the mucus discussed below. As mucus moves through a stented airway, it has a tendency to accumulate at the ends of the stent. This may be due to a number of factors including the inability of the trachea/bronchi to compress enough to produce an airflow with sufficient force or velocity to move the mucus through the stented area because, e.g., the stent may prevent or inhibit radial compression or other constriction of the airway.

Some stents include a coating (e.g., a polymer coating) that can act as a barrier to tumor ingrowth. However, the choice of material and/or surface structure of the coating can influence, for example, the adherence of mucus to the coating.

Some attempts have been made to reduce accumulation of mucus in stents. For example, lubricious hydrophilic coatings of stent inner lumens have been formulated for the purpose of promoting mucus transport and to aid in the prevention of mucus buildup. (See, e.g., Merit™ Aero® fully covered tracheobronchial stent at http://endotek.merit.com/products/pulmonary.aspx (last visited Mar. 13, 2013).) However, in some circumstances, the use of hydrophilic materials has promoted mucus attachment, thereby increasing mucus accumulation, as well as the likelihood of airway plugging and infection.

Thus, there exists a desire for improved medical devices that reduce or eliminate one or more deficiencies of previous medical devices. For example, improved medical devices that reduce accumulation of mucus in a stented airway are desired. Improving one or more of the factors that facilitate movement of mucus through an airway may be useful to reduce or eliminate mucus accumulation. Improved medical devices that reduce or prevent mucus attachment and/or accumulation and thus reduce or eliminate the likelihood of an infection are desired.

The issue of mucous transport is one of many issues associated with placing an implant inside the body. Another issue associated with placing an implant inside the body is the patient's risk for infection, and or allergic reactions. Typically, given the nature of processing medical device components, the surface energy of such components is generally fairly high allowing most bodily fluids to wet on them. This can cause bacterial cultivation leading to infection.

It would be desirable to provide a medical device for implantation in the body that has been engineered to reduce the risk of infection and/or allergic reaction.

Yet another issue associated with placing an implant inside the body involves adhering the implant to the surrounding tissue. There is a need to provide implanted devices with features which will prevent the implant from migrating or at least reduce any possible migration.

Without limiting the scope of the present disclosure, a brief summary of some of the claimed embodiments of the present disclosure is provided below. Additional details of the summarized embodiments and/or additional embodiments of the present disclosure can be found in the detailed description.

A brief abstract of the technical disclosure in the specification is provided as well for the purposes of complying with 37 C.F.R. 1.72. The abstract is not intended to be used for interpreting the scope of the claims.

All US patents and applications, and all other published documents mentioned anywhere in this application, are incorporated herein by reference, each in its entirety.

SUMMARY

In one or more aspects of the present disclosure, a method for reducing mucus accumulation in an airway may include disposing an implantable device (e.g., a stent, etc.) within an airway (e.g., a pulmonary airway, a main bronchus, a trachea, etc.), wherein the implantable device has a first end, a second end, and an inner surface defining a lumen extending from the first end to the second end. In one or more embodiments, at least a portion of the inner surface may be hydrophobic (e.g., may include a superhydrophobic microstructure) and has dynamic water contact angles of 145 degrees or greater. In one or more embodiments, the implantable device may be constructed and arranged to maintain patency of the airway and accumulation of mucus may be reduced as compared to a similar implantable device without the hydrophobic portion of the inner surface.

In another aspect of the present disclosure, an implantable medical device may include an airway stent having a first end, a second end, and an inner surface defining a lumen extending from the first end to the second end. In one or more embodiments, a coating may be disposed over at least a portion of the inner surface, wherein a coating surface may be hydrophobic (e.g., superhydrophobic) and has dynamic water contact angles of 145 degrees or greater (e.g., at least 160 degrees, from 160 degrees to 170 degrees, etc.). In one or more embodiments, the implantable medical device may have reduced adhesion with aqueous material and mucus material as compared to a similar stent without the coating. In at least one embodiment, the airway stent may be structured and arranged to maintain the patency of an airway. In one or more embodiments, a hydrophobic coating surface may be disposed proximate (e.g., near) at least one of the first and second end and may even extend from the first end to the second end.

In one or more aspects of the present disclosure, a method for promoting transport of mucus in an airway may include disposing an implantable medical device as described herein in an airway. In another aspect of the present disclosure, a method for reducing inflammation at an implantation site may include disposing an implantable medical device as described herein at an implantation site in an airway.

In another aspect of the present disclosure, a method for making an implantable device having a superhydrophobic surface may include providing an airway stent having a first end, a second end, and an inner surface defining a lumen extending from the first end to the second end. The method may also include disposing on the airway stent a surface that is hydrophobic (e.g., superhydrophobic) and has dynamic water contact angles of 145 degrees or greater. In one or more embodiments, disposing a hydrophobic surface on the airway stent may include disposing a polymer coating on at least the inner surface of the airway stent and forming a hydrophobic microstructure on the coating by one or more techniques including laser ablation, photolithography-based microfabrication, solidification of melted alkylketene dimer, microwave plasma enhanced chemical vapor deposition of trimethoxylmethoxysilane, phase separation, and domain selective oxygen plasma treatment. In one or more embodiments, disposing a hydrophobic surface on the airway stent may include disposing a polymer coating on at least the inner surface of the airway stent and forming a hydrophobic microstructure on the coating by one or more techniques including roughening an outer surface of a mandrel, placing an airway stent on the mandrel, applying a polymeric material to the airway stent and mandrel, and curing the polymeric material to form the hydrophobic surface (e.g., superhydrophobic) in the form of an airway stent coating.

BRIEF DESCRIPTION OF THE FIGURES

The present disclosure and the following detailed description of certain embodiments thereof can be understood with reference to the following figures.

DETAILED DESCRIPTION

Figure 1:
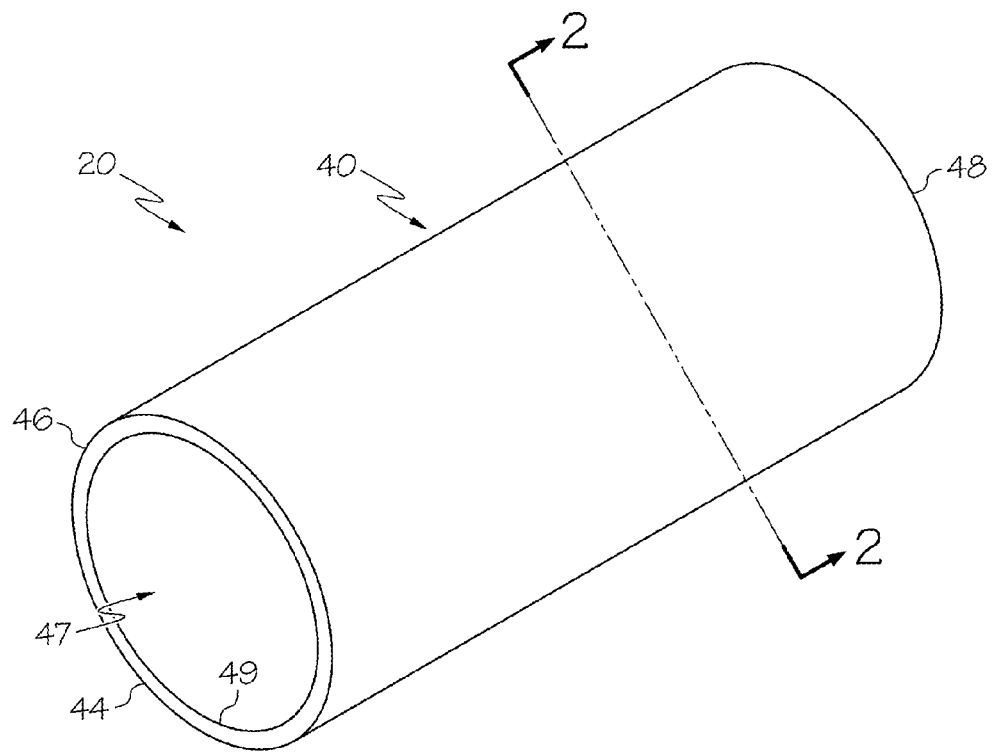
FIG. 1 is a schematic of a medical device.

While the subject matter of the present disclosure can be embodied in many different forms, specific embodiments of the present disclosure are described in detail herein. This description is an exemplification of the principles of the present disclosure and is not intended to limit the present disclosure to the particular embodiments illustrated.

For the purposes of this disclosure, like reference numerals in the figures, shall refer to like features unless otherwise indicated.

Various aspects of the present disclosure are depicted in the figures. Elements depicted in one figure can be combined with and/or substituted for elements depicted in another figure, as desired.

In one or more aspects of the present disclosure, a method for reducing mucus accumulation in an airway includes disposing an implantable device within an airway. In one or more embodiments, the implantable device includes an airway stent (e.g., an airway stent) and is constructed and arranged to maintain patency of an airway. In one or more embodiments, the airway in which the implantable device may be disposed can be a main bronchus, a trachea, and/or any other location within an airway, without limitation.

Figure 2:
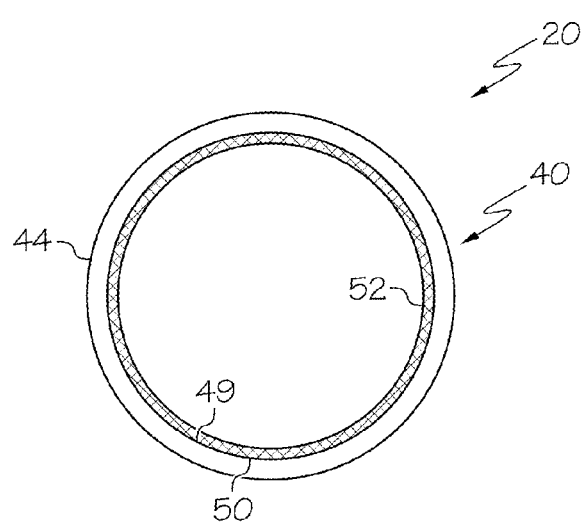
FIG. 2 is a cross-section of the medical device of FIG. 1 taken along 2-2.

In one or more embodiments, with reference to FIG. 1, an implantable device, shown schematically at 20 can include a stent 40 having an inner surface 49, an outer surface 44, a first end 46, and a second end 48. Lumen 47 extends from the first end 46 to the second end 48. As shown in FIG. 2, a cross-section of FIG. 1, inner surface 49 has a coating 50 thereon. Coating 50 has a coating inner surface 52.

The implantable device shown schematically in FIGS. 1 and 2 may be self-expanding, balloon expandable, or hybrid expandable. Embodiments of the medical device may have a constant diameter, tapers, flares and/or other changes in diameter in the body (e.g., between the ends) and/or at an end.

In some embodiments, the medical device may include a stent having a coating on the interior surface and, optionally, the outer surface. In some embodiments, the medical device may include a stent having a liner on the inner surface and, optionally, the outer surface.

Coating 50 may be disposed about at least a portion of the inner surface 49 and, typically, the entire inner surface. In at least one embodiment, the coating 50 substantially covers the entire inner surface 49 of the expandable stent 40. In other embodiments, the coating 50 covers less than the entirety of the inner surface 49 of the expandable stent 40.

As shown in FIG. 2, the coating 50 can be directly connected to the inner surface 49 of the expandable stent 40. In one or more embodiments, the polymeric coating 50 can be connected to the inner surface 49 of the expandable stent 40 using an adhesive or other means of attaching the coating to the device. In at least one embodiment, the coating at least partially covers the outer surface 44 also. In at least one embodiment, partial coverage can include partial coverage of the perimeter and/or the length. In some embodiments, the coating 50 and the stent 40 can be integral (e.g., collectively formed as an integral construction). For example, in one or more embodiments in which at least a portion a stent 40 is made of a material (e.g., silicone, silicone coating, biocompatible polymer or metal, etc.) appropriate for micropatterning, then the micropattern may be directly incorporated into the structure of the stent 40 (e.g., the stent 40 and polymer coating 50 having a micropattern can be integrally formed).

Figure 3:
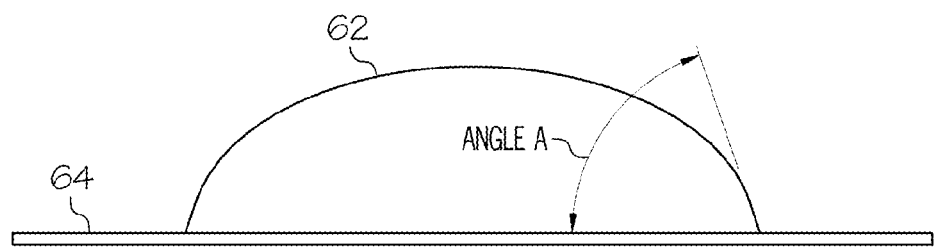
FIGS. 3 and 4 depict a drop on a surface.
Figure 4:
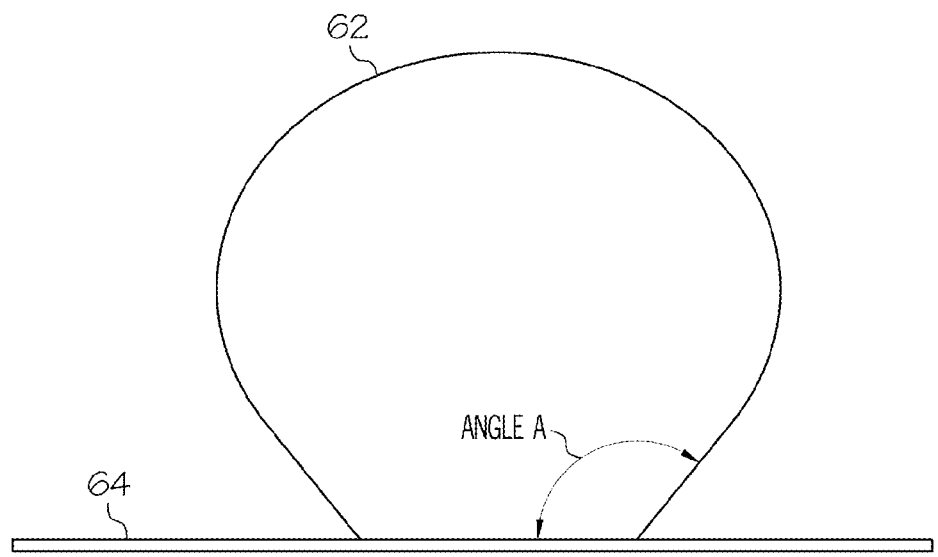

In one or more embodiments, at least a portion of the inner surface has a hydrophobic polymer coating thereon, wherein a polymer coating surface has dynamic water contact angles of 145 degrees or greater. For example, a stent may have a polymer coating thereon, wherein a polymer coating surface has dynamic water contact angles of 145 degrees or greater. In some embodiments, the water contact angles may be greater than 150 degrees, greater than 160 degrees, greater than 165 degrees, or greater than 170 degrees. In some embodiments, the water contact angle may be from 150 degrees to 175 degrees, from 150 degrees to 170 degrees, from 160 degrees to 170 degrees, etc. The water contact angle (i.e., the angle at which a liquid meets a surface) is illustrated in FIGS. 3 and 4. FIGS. 3 and 4 show a drop 62 on a surface 64. The water contact angle 'a' is shown in FIG. 3. In FIG. 3, angle 'a' is less than 90 degrees whereas in FIG. 4, water contact angle 'a' is 145 degrees. The sessile drop technique as described in standard surface chemistry textbooks is suitable for measuring a static or a dynamic water contact angle.

In one or more methods of the present disclosure, accumulation of mucus is reduced as compared to a similar implantable device without the hydrophobic portion of the inner surface. That is, in a comparison of (1) a given implantable device having a hydrophobic coating surface thereon with (2) the same device lacking the hydrophobic coating surface, the former would be have a reduced accumulation of mucus (e.g., when implanted in an airway of a patient).

For purposes of the present disclosure, a hydrophobic surface is one that has a static water contact angle of greater than 90 degrees. A superhydrophobic surface is one what has a dynamic (receding or advancing) water contact angle greater than or equal to 145 degrees.

In one or more embodiments, the hydrophobic polymer coating 50 includes a superhydrophobic microstructure formed on the polymer coating surface 52. Exemplary superhydrophobic microstructures may include those described in Weber (U.S. Pat. App. Publ. No. 2007/0005024 A1 (Weber et al.)) and the documents cited therein, all of which are incorporated herein by reference, each in its entirety.

In one or more methods of the present disclosure, disposing the implantable device within the airway includes disposing the implantable device within a pulmonary airway. Any of a wide variety of delivery methods, without limitation, may be suitable to dispose an implantable device within an airway. Any of a wide variety of stent delivery devices may be suitable to dispose an implantable device within an airway.

An implantable device of the present disclosure may be implanted (e.g., deployed) within any pulmonary airway (e.g., a main bronchus, a trachea, etc.).

In one or more aspects of the present disclosure, an implantable medical device can include an airway stent and a coating disposed over at least a portion of the airway stent inner surface. In at least one embodiment, the airway stent is constructed and arranged to maintain the patency of an airway (e.g., an airway lumen, such as a main bronchus or trachea).

In at least one embodiment, a coating surface 52 is hydrophobic and has dynamic water contact angles of 145 degrees or greater (e.g., 150 degrees or greater, 160 degrees or greater, 165 degrees or greater, 170 degrees or greater, from 150 degrees to 175 degrees, from 150 degrees to 170 degrees, from 160 degrees to 170 degrees, etc.). In one or more embodiments, due at least in part to the superhydrophobicity of the coating surface 52, an implantable medical device (e.g., an airway stent) has reduced adhesion with aqueous material and mucus material as compared to a similar stent without the coating 50 (e.g., without the coating surface 52).

As described herein, mucus may tend to accumulate in the vicinity of stent ends. To reduce mucus accumulation, it may be useful to position a hydrophobic coating surface 52 near at least one of the first end and the second end. For example, a coating surface may longitudinally extend from the first end 46 to the second end 48. In one or more embodiments, the coating surface 52 may longitudinally extend from either the first end 46, the second end 48, or both for a longitudinal distance of less than 50% of the airway stent length (e.g., less than 40%, less than 30%, less than 20%, less than 10%, etc.). In at least one embodiment, the polymer coating 50 (e.g., the hydrophobic coating surface 52) covers substantially all of the inner surface of the stent 40 (i.e., from the first end 46 to the second end 48).

One or more aspects of the present disclosure relates to a method for promoting transport of mucus in an airway. The method includes disposing an implantable medical device (e.g., implantable medical device 20), as described herein, in an airway.

One or more aspects of the present disclosure relates to a method for reducing inflammation at an implantation site. The method includes disposing an implantable medical device (e.g., implantable medical device 20), as described herein, in an airway. In one or more embodiments, a reduction of accumulation of mucus at the implantation site (e.g., an airway) can cause a resultant reduction of inflammation of the implantation site tissue, particularly at or near the ends of the implantable medical device.

One or more aspects of the present disclosure relates to a method for making an implantable device having a superhydrophobic surface. The method includes providing an airway stent having a first end, a second end, and an inner surface defining a lumen extending from the first end to the second end. The method further includes disposing on the inner surface of the airway stent a surface that is hydrophobic and has dynamic water contact angles of 145 degrees or greater.

In one or more embodiments, disposing on the airway stent or any other stent or suitable medical device a surface may include attaching (e.g., adhering, bonding, connecting, etc.) a polymer coating that has a polymer coating surface that is superhydrophobic. In one or more embodiments, the method includes disposing a polymer coating 50 on at least the inner surface of the airway stent 40 and forming a superhydrophobic microstructure on the coating 50. Forming a superhydrophobic microstructure on the coating may be accomplished any of a wide variety of techniques including, but not limited to, laser ablation, photolithography-based microfabrication, solidification of melted alkylketene dimer, microwave plasma-enhanced chemical vapor deposition of trimethoxylmethoxysilane, phase separation, and domain selective oxygen plasma treatment. The method may alternatively include roughening an outer surface of a mandrel, depositing polymer material on the mandrel, placing the polymer material on an airway stent or any other stent or suitable medical device so that the inner surface of the stent or medical device contacts the polymer material, such that the polymer material is transferred to the inner surface of the stent.

In one or more embodiments, mucus transport may be promoted by, for example, reducing the surface energy of an airway lumen wall, such as an interior surface of an airway stent coating. Because as mentioned herein, mucus transport depends at least in part on the adherence of the mucus to the airway lumen wall, providing a superhydrophobic surface on the interior surface (e.g., inner surface of the airway stent or other stent, inner surface of a stent coating, etc.) should facilitate mucous transport.

In one or more embodiments, the hydrophobic coating may be applied on all or a portion of the inner surface of a stent coating. In some embodiments, the hydrophobic coating may be present on the inner surface of a stent, but not the outer surface of the stent where a hydrophobic coating may promote undesirable stent migration. However, because stent migration may be otherwise controlled by any manner known to one of skill in the art (e.g., use of fixation anchors, barbs, flares, etc.), the present disclosure contemplates use of the hydrophobic coating on any or all surfaces of a stent, including the outer surface.

Although not wishing to be bound by theory, surface energy or wettability quantifies the disruption of intermolecular bonds that form when a surface is created. Wettability may be demonstrated by a contact angle measurement of a drop of water on the surface. For example, when the contact angle is small (e.g., below 45 degrees) the surface material is said to be hydrophilic and thus can provide a surface that has good wettability (droplet spreads out on surface). When the contact angle is above 90 degrees, for example, the surface material is said to be hydrophobic and thus has poor wettability (e.g., the surface repels liquids, droplets remains spherical).

Thus, a hydrophobic coating having poor wettability may reduce or prevent mucus buildup, relative to a hydrophilic coating that has high wettability.

In some embodiments, even the hydrophobic materials may accumulate mucus to some extent. In one or more embodiments, a superhydrophobic coating may further reduce the accumulation of mucus.

In at least one embodiment, a micropatterned polymer coating can be applied to a stent or other suitable medical device to create a super hydrophobic surface (e.g., lowering the surface energy of the surface of the stent to the extent that the dynamic water contact angle created is 145 degrees or greater) that can be useful in that the surface promotes fluid movement (e.g., fluids such as mucus and water are less likely to attach to the stent, which helps reduce or prevent inflammation, granulation tissue formation, and/or mucous plugging) and is self-cleaning (e.g., bacteria has greater affinity for aqueous fluids and leave the stent surface with droplets of aqueous fluids as they roll off).

A lotus leaf is a natural example of a surface that is superhydrophobic. Although not wishing to be bound by theory, the increased ability of a lotus leaf to repel water depends in part on architecture of the lotus leaf surface. On a microscopic or nanoscopic scale, the surface of the lotus leaf includes closely-packed papillae structures. The spacing of these papillae allows a large extent of air trapping when contacting a liquid such as water. The microstructure present on the lotus leaf surface, in conjunction with the low surface energy of the lotus leaf material, provides a superhydrophobic surface having a contact angle upwards of 160-170 degrees. This, in conjunction with the already low surface energy of the material creates a superhydrophobic surface with a contact angle of at least 145 degrees or more, and desirably, upwards of 160-170 degrees. Superhydrophobicity, in some embodiments, may also create a self-cleaning surface as demonstrated by the lotus leaf.

In comparison, upon contact with water, polypropylene's contact angle has been reported to be about 105 degrees, silicone's contact angle has been reported to be about 110 degrees, PET's contact angle has been reported to be about 75 degrees, polyurethane's contact angle has been reported to be about 85 degrees, and PTFE's contact angle has been reported to be about 115 degrees.

Numerous methods of producing superhydrophobicity of a polymer surface have been developed. For example, in one or more embodiments, a microstructure may be etched on a coating surface.

In one or more embodiments, a superhydrophobic polymer coating may be manufactured by laser etching a pattern on a coating mandrel, placing a stent on the mandrel, dipping or spraying the stent, and allowing the coating to mimic the pattern and cure in that formation. In at least one embodiment, the superhydrophobic coating can be manufactured by roughening the surface of a mandrel with sand paper.

In one or more embodiments, a microstructure can be created by coating a stent or other suitable medical device on a standard mandrel and performing a secondary operation on the inner diameter of the stent or other suitable medical device (e.g., laser ablation, photolithography-based microfabrication, solidification of melted alkylketene dimer, microwave plasma-enhanced CVD of trimethoxylmethoxysilane, phase separation, or domain-selective oxygen plasma treatment (surface doping within a plasma treatment chamber), etc.).

The following documents relate to techniques for manufacturing a micropatterned surface, each of which is incorporated by reference in its entirety: Kroetch, "NanoFab's PDMS Microfluidic Device Fabrication Manual," September 2004, 8 pgs. (available online at http://www.nanofab.ualberta.ca/wp-content/uploads/2009/03/boxedpdms.pdf, last accessed Mar. 10, 2013); Dodou et al., "Mucoadhesive micropatterns for enhanced grip," Conf. Proc. IEEE Eng. Med. Biol. Soc., 2007; 2007:1457-62; Kwon et al., "Friction enhancement via micro-patterned wet elastomer adhesives on small intestinal surfaces," Biomed. Mater., 2006 December; 1(4):216-20; Tooley et al., "Thermal fracture of oxidized polydimethylsiloxane during soft lithography of nanopost arrays," J. Micromech. Microeng., 2011, 21:054013 (9 pgs.); and Desai et al., "Plastic masters-rigid templates for soft lithography," Lab Chip, 2009 Jun. 7; 9(11):1631-7.

In one or more embodiments, the microstructure may be designed having topology and dimensions that are similar to the papillae of a lotus leaf. In at least one embodiment, the stent having a superhydrophobic polymer coating will have a reduced surface energy (e.g., relative to a polymer coating lacking a microstructure) resulting in reduced mucus buildup in the airway.

Articles having superhydrophobic surfaces are described by Weber et al. (U.S. Pat. Appl. Pub. No. 2007/0005024 A1), Gelbart et al. (U.S. Pat. Appl. Pub. No. 2008/0226694 A1), and Edin (U.S. Pat. No. 8,043,359), Privett et al. (PCT Int'l Pat. App. WO 2012/167017 A2), Atanasoska et al. (U.S. Pat. Appl. Pub. No. 2009/0294732), Taton et al. (PCT Int'l Pat. Appl. Pub. No. WO 2010/033482), and Jin et al. (PCT Int'l Pat. Appl. Pub. No. WO 2010/022107), each of which is incorporated by reference in its entirety. In particular, techniques for providing superhydrophobic surfaces are provided at paragraphs [0040]-[0063] of Weber et al. (U.S. Pat. Appl. Pub. No. 2007/0005024), incorporated by reference herein.

In one or more embodiments, a stent having a hydrophobic coating can be useful in reducing mucus accumulation and related complications (e.g., infection, inflammation, etc.).

In one or more embodiments, a micropatterned polymer coating may be applied to a medical device (e.g., an implantable medical device) in order to, for example, reduce the interaction of medical device materials with biological tissue that may experience an inflammatory and/or allergic response. In particular, a hypoallergenic micropatterned polymer coating may be useful when the coating is a component of a medical device (e.g., an implantable medical device) that may spend a duration of time in contact with biological tissue (e.g., a mucosal wall).

Figure 5:
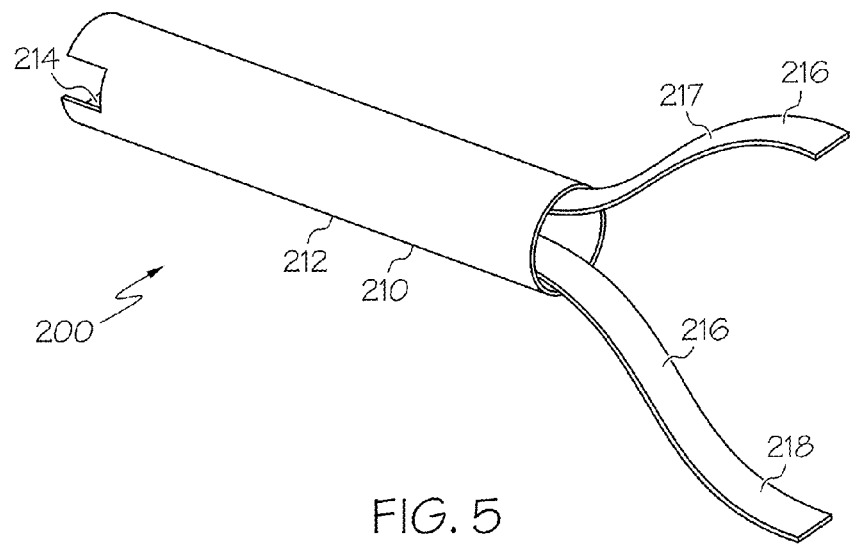
FIG. 5 shows a perspective view of a medical device.

Application of a micropatterned polymer coating on a medical device may be accomplished by, for example, a chamber-style process in order to treat all exposed surfaces with either a micropatterned polymer coating or utilizing a doped plasma chamber to create microstructure on the surface of a medical device material (e.g., an alloy, etc.). For example, a portion of a medical device is depicted in FIG. 5 wherein a superhydrophobic coating or etching may be performed on all surfaces of the medical device. Hemostasis clip 200 includes tube 210 with an outer surface 212 and an inner surface 214. One or more arms 216 extend from the tube. Arms 216 have an outer surface 217 and an inner surface 216. A superhydrophobic coating may be disposed on the exterior and/or interior of tube 210 and/or on the outer surface and/or inner surface of arms 216. The entirety of one or more surfaces may be provided with a superhydrophobic coating or a portion which is less than the entirety of the surface may be provided with such a coating. More desirably, the arms have an outer surface with a superhydrophobic coating to facilitate movement in and out of the tube and an inner surface with an antimigratory coating to facilitate grasping.

The medical device can be a stent, a catheter, a valve, a clip, a closure device, or any other suitable medical device which is placed in the body or implanted in the body.

In one or more embodiments, a micropatterned polymer coating is disposed on some, but not all, of the surfaces of a medical device.

Micropatterned polymer coatings may be formed from and/or include one or more of a wide variety of polymers including, but not limited to polytetrafluoroethylene (PTFE), polypropylene, acrylic polymers and nitrile butadiene. All of these polymers may be deposited in a manner which may decrease surface energy to a level of hydrophobicity and desirably, superhydrophobicity. In addition, the hypoallergenic nature of these polymers may be useful when covering materials (e.g., alloys) known to cause allergic reactions.

The present disclosure is also directed to the use of a micropatterned structure on an implantable medical device to provide different sections or levels of adhesiveness to the lumen wall. Devices provided with such a micropatterned structure may be used in any suitable lumen, or passageway in the body, including the airway.

Research has been conducted in the area of using micropatterned adhesives in wet biological applications. For example, applications of this research include endoscopic robots and biodegradable tissue adhesives. (See, e.g., Lotters et al., "The mechanical properties of the rubber elastic polymer polydimethylsiloxane for sensor applications," J. Micromech. Microengineering, 1997, 7(3):145-147; Axisa et al., "Low cost, biocompatible elastic and conformable electronic technologies using MID in stretchable polymer," Conf. Proc. IEEE Eng. Med. Biol. Soc., 2007; 2007:6593-6; Jeong et al., "Nanohairs and nanotubes: Efficient structural elements for gecko-inspired artificial dry adhesives," Nano Today, August 2009, 4(4):335-346; and Majidi, "Enhanced Friction and Adhesion with Biologically Inspired Fiber Arrays," University of California, Berkeley, Ph.D. thesis, May 15, 2007, 143 pgs, all of which are incorporated by reference, each in its entirety) Although not wishing to be bound by theory, the mechanism for micropattern attachment to tissue (e.g., the digestive tract) may be based on the ability of the tissue to conform to the micropatterned surface and interlock with it in these applications. As a result, architectures have evolved to less-closely resemble the hair-like structures found on the feet of a gecko. For example, by decreasing pillar density and aspect ratio, it is possible to achieve greater pillar-tissue interlock, as discussed in Mandavi et al., "A biodegradable and biocompatible gecko-inspired tissue adhesive," Proc. Natl. Acad. Sci. U.S.A., 2008 Feb. 19; 105(7):2307-12, incorporated herein by reference in its entirety.

Soft lithography techniques can also be used to produce the disclosed device coating in general and stent coating in particular. These methods involve accurately replicating micro- and nano-scale features onto soft, elastomeric materials by casting polymer over a micropatterned silicon wafer master mold. Consistent and replicable micropillars have been produced this way. Additional precautions, including double casting methods or use of interim plastic masters, can also be taken to reduce the stress applied to the micropillars during manufacture in order to better maintain pillar integrity and overall pattern function.

Micropillars have been fabricated using a variety of polymeric materials. Indeed, any polymeric material can be used to create a micropatterned adhesive provided it is flexible enough conform to the target tissue type and create an effective interlock. In addition to providing anti-migration properties that promote tissue interlock for increased traction against the lumen wall, this micropattern can also be applied to the medical device in general or stent in particular to create a super hydrophobic surface. In essence, lowering the surface energy of the medical device in general or stent in particular to the point where the contact angle created is greater than 145 degrees or more, and, more desirably, 150 degrees or more can provide a surface that promotes fluid movement. To that end, as discussed above, mucus and water is less likely to attach to a medical device or stent in particular with such a surface which helps prevent inflammation, granulation tissue formation, and mucus plugging. Such a surface may also be self-cleaning. Because bacteria have a greater affinity for water, it will latch onto droplets as the droplets roll off the medical device in general and stent in particular.

The surface is desirably made of closely packed papillae structures. The spacing of these papillae brings a large extent of air trapping when contacting a liquid such as water. This, in conjunction with the already low surface energy of the material creates a superhydrophobic surface with a contact angle 145 degrees or greater, more desirably 160 degrees or greater and even more desirably, 170 degrees or greater. As discussed above, the superhydrophobicity may also create a self-cleaning surface.

In one embodiment, a surface is engineered to reduce the collection of bacteria thereon. Specifically, a superhydrophobic surface is provided using any of the techniques disclosed herein. The surface is desirably an inner surface of an airway stent or a gastrointestinal stent. The surface may be of silicone or any suitable material, polymeric or otherwise. The surface is, optionally, in the form of a coating.

One way to accomplish this pattern is by laser etching the specific pattern onto a coating mandrel. When the medical device in general or stent in particular is placed on the mandrel and dipped or sprayed, the coating will mimic the pattern and cure in that formation. The pattern can also be accomplished by roughening the surface of the mandrel with sand paper as well. Other ways to create the microstructure involve coating the medical device in general or stent in particular on a standard mandrel and then performing a secondary operation on the inner and/or outer diameter such as laser ablation, photolithography-based microfabrication, solidification of melted alkylketem dimmer, microwave plasma enhanced CVD of trimethoxylmethoxysilane, phase separation, or domain-selective oxygen plasma treatment (surface doping within a plasma treatment chamber).

Figure 6A:
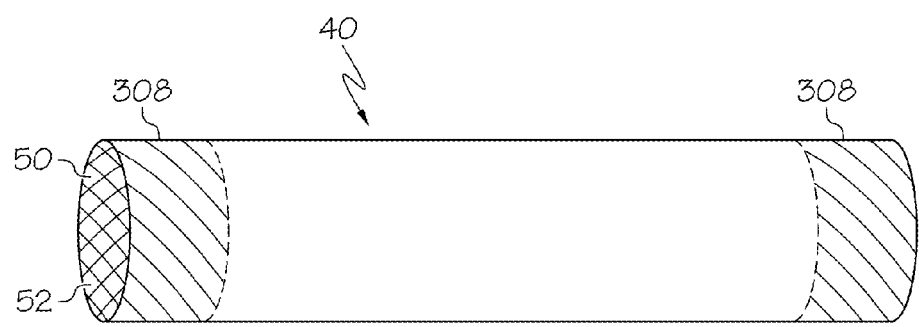
FIG. 6A shows a schematic of a stent.

It is within the scope of the present disclosure to combine two patterns on the outside of the coating. As shown in FIG. 6A, an anti-migration micropattern 308 is applied, by any of the means described above, to the outer edges of the medical device in general or stent 40 in particular. A superhydrophobic pattern 52 is applied throughout the inner portion as shown in FIG. 6A. Micropattern 308 on the outer edges will aid in migration prevention. Interlocking the pattern with the mucosal wall will create enhanced traction and keep the stent from moving out of position, essentially promoting tissue ingrowth without the concern of removability. The inner micropattern 52 will greatly aid in the movement of fluid through that portion. This will help prevent any excess buildup around the stent and allow proper clearance of mucus and water. To further enhance this effect, micro sized holes can be strategically placed within the pillars of the micropattern to promote further fluid drainage.

Figure 6B:
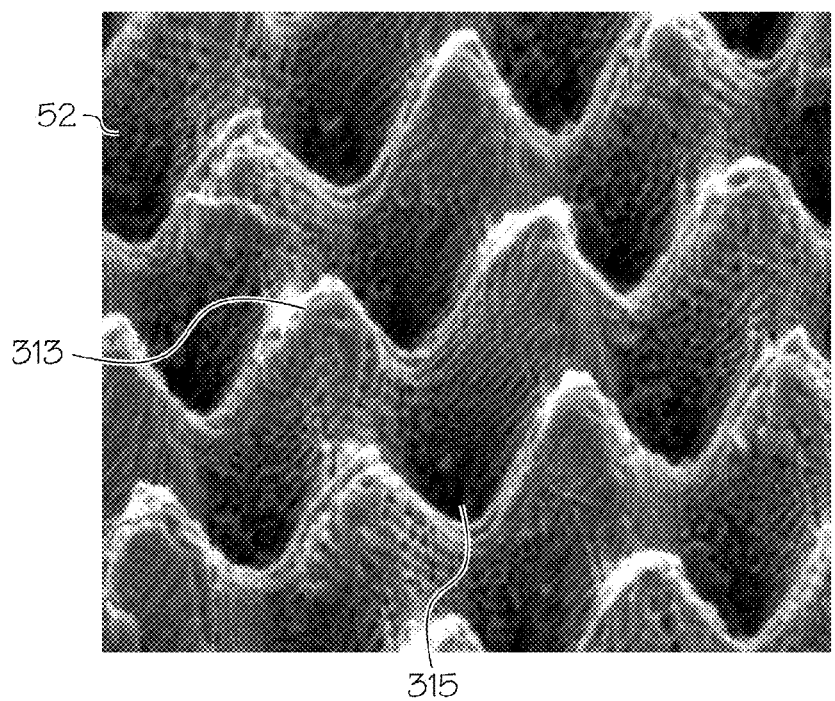
FIG. 6B shows a micropattern with protrusions.

Desirably, as shown in FIG. 6B, micropattern 52 will be in the form of a plurality of protrusions, such as pillars 313. Optionally, the micropattern may include one or more drainage holes 315 to facilitate fluid movement.

Figure 6C:
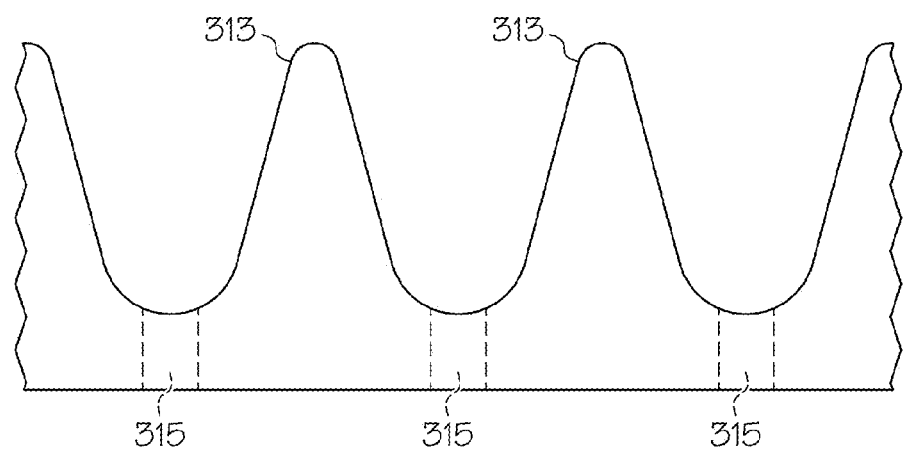
FIG. 6C shows a micropattern with drainage holes.

FIG. 6C shows a micropattern 52 with pillars 313 and drainage holes 315. Desirably, the drainage holes will have opening of from 10 microns to 20 microns across. Smaller or larger openings may also be used. The pillars may be less than 1 micron across (for example, 0.3 microns), or they may be from 1 to 10 microns across or larger. The holes may be used to drain mucus or other fluids to allow traction to be maintained during fluidic exchange.

The micropattern shown in FIG. 6C may be applied on the surface, desirably, the outer surface, of a stent, for example, a braided or other stent, to allow mucus through the stent and maintain traction on the outside of the stent.

This treatment will also enhance stent flexibility through a slippery surface and tissue ingrowth prevention. While it helps with fluid drainage as stated above, the extremely low surface energy will also help prevent tissue ingrowth along the middle portion of the stent. This will allow the stent to easily extend and compress axially within the two anti-migration portions. This is particularly useful for stents used in the trachea and bronchus where movement occurs during a cough, swallow, and forced ventilation. The ability of a stent to flex and match such movement is important in preventing migration. A stiff stent is likely to migrate when the trachea expands and contracts. If the stent is flexible, it can move in conjunction with the trachea and be more likely to remain in place.

Figure 7:
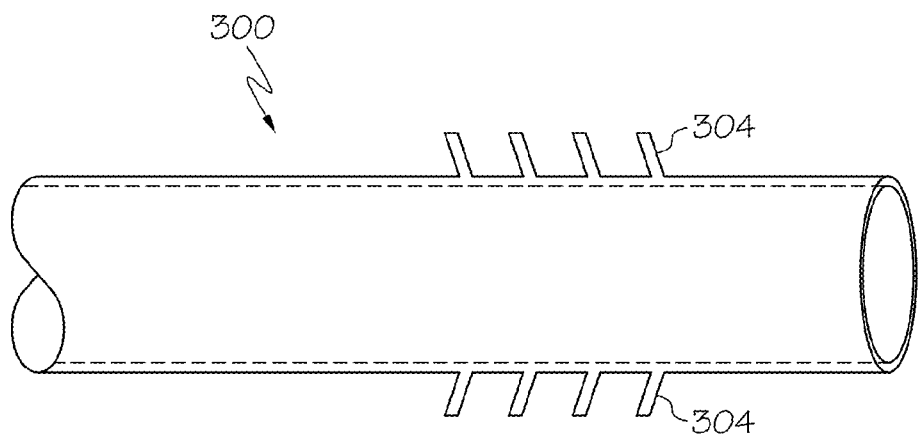
FIG. 7 shows a schematic of a stent with a micropattern of pillars.
Figure 8:
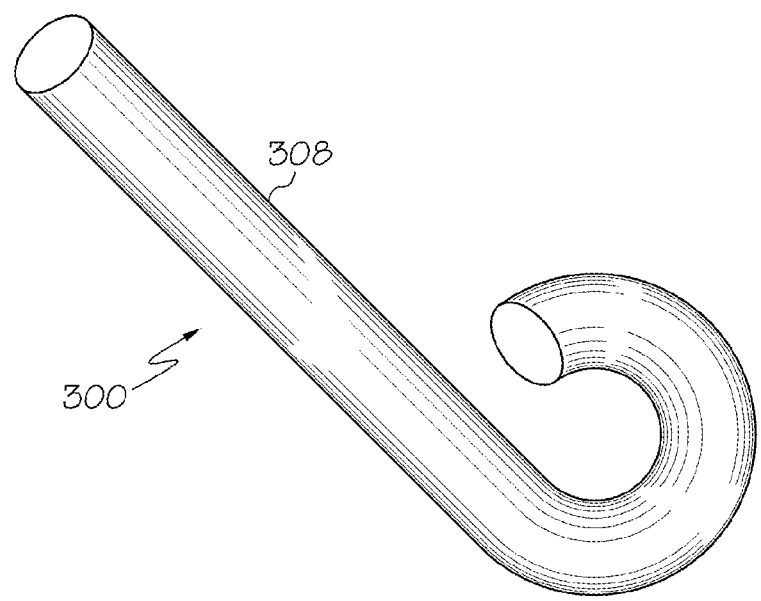
FIG. 8 shows a pancreatic stent with a micropattern.

The micropatterns may be applied to implantable medical device other than stents for use in the respiratory system. It may also be applied to stents that are placed in other vessels in the body such as a biliary stent or an airway stent. With respect to a biliary stent or airway stent, the pillars of the micropattern may be oriented in one direction to increase anti-migratory effects. For biliary/pancreatic stents, this could eliminate the need for anti-migratory "pegs" that are cut from the stent wall. An example of this is shown in FIG. 7. Stent 300, shown schematically in FIG. 7, includes a micropattern of pillars 304 which is oriented in one direction. FIG. 8 shows pancreatic stent 300 with a micropattern 308.

In at least one embodiment, for example, that shown in FIG. 7, a micropattern may include protrusions (e.g., micropillars or other suitable shapes) that are oriented in a direction that is not perpendicular to a base. For example, one or more micropillars may extend from a base a first distance from the base in a direction perpendicular to the base and a second distance in a direction parallel to the base. In one or more embodiments, the micropillars are arranged in a diagonal configuration, wherein each micropillar extends in a direction parallel to that of the other micropillars. Herein, "one-way" micropattern includes a plurality of microstructures that extend a first distance from the base in a direction perpendicular to the base and a second distance in a direction parallel to the base. In one or more embodiments, a one-way micropattern may replace or supplement traditional antimigration features on stents, such as pegs. The use of a one-way microstructure can, in some embodiments, reduce trauma to a body lumen wall while reducing or eliminating stent migration.

In one or more embodiments, the protrusions in the superhydrophobic region may be spaced 100 microns apart and may be 50 microns wide and have a height of 150 microns. In other embodiments, the protrusions in the superhydrophobic region may be spaced 50-100 microns apart and may be 25-50 microns wide and have a height of 100-200 microns. Typically, the spacing between adjacent protrusions will exceed the width of the individual protrusions, desirably by a factor of two or more. In other embodiments, other sizes and spacing of protrusions may be employed.

Figure 9:
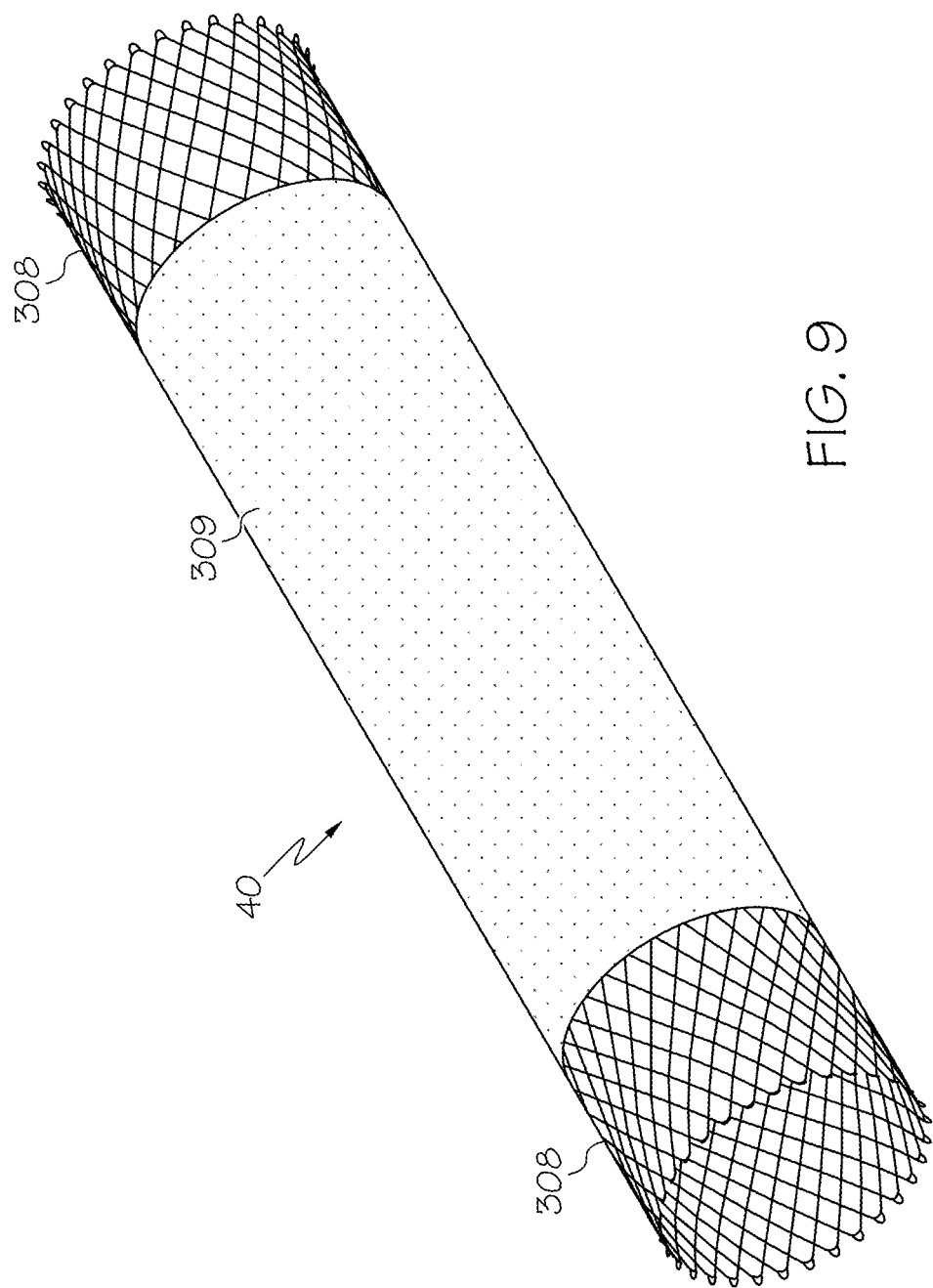
FIG. 9 shows a schematic of a stent.

The present disclosure is also directed to a stent such as that shown in FIG. 9. Stent 40 includes one or more regions 308 with a micropattern and/or an exposed stent having openings. As shown in FIG. 9, stent 40 has regions 308 at both ends. Micropattern 308 is arranged to provide in-growth. Region 309 is provided with a superhydrophobic surface to prevent in-growth in the region.

The present disclosure is further directed to a stent or other suitable medical device with a dual coating. The outside is provided with a high-friction and/or high adhesion region, desirably to prevent migration. The inside is provided with a surface arranged to prevent biofilm formation and/or bacteria adhesion. The inner surface may be hydrophilic in some embodiments. Desirably, however, it will be hydrophobic and more desirably, superhydrophobic. The inner and/or outer surfaces may be in the form of a coating.

The present disclosure is also directed to a stent, typically plastic, with a micropattern on the outside to aid in removal of the stent. The present disclosure is also directed to a stent, typically plastic, with a micropattern on the outside to help anchor it in the vessel.

The present disclosure is further directed to a stent with an interior having one or more regions which are superhydrophobic. This may be used, for example, to prevent bile buildup and/or to lower the friction and/or deployment force. The increased contact angle associated with the superhydrophobic region would enhance drainage through the stent. Desirably, the superhydrophobic region on the inner surface of the stent would lower tracking force as the stent is delivered to its target site.

The present disclosure is also directed to applying a spray which provides a micropatterned surface to the inner wall of a vessel such as the esophagus or colon. Alternatively, a sleeve with a micropatterned surface may be used. The micropatterned surface may be any of those disclosed herein which provide for greater adhesion to the surface of a bodily vessel. The spray or sleeve may be used in conjunction with a stent. The stent optionally may be provided with a similar micropattern to allow for adhesion to the wall or to the sleeve. The interior of the stent optionally may be provided with a superhydrophobic surface.

In one or more embodiments, a double layer micropattern polymer coating may be formed by, for example, spray coating a lining of a micropatterned mold (e.g., micropattern sphere such as a Velcro ball, object) or a body lumen (e.g., an esophagus, a colon wall, etc.) to fill the voids and contact wall, followed by deploying a device (e.g., a stent) with a micropattern to connect with (e.g., adhere to) the spray coat.

In another embodiment, the present disclosure is directed to a jejunal liner which may be used, for example, to treat obesity. The liner may be in the form of a sleeve that may be anchored in the pylorus. The sleeve may prevent food absorption in the duodenum and part of the jejunum. Any of the micropatterns (e.g., adhesive micropatters, etc.) disclosed herein for reducing migration and/or increasing adhesion may be provided to outer surface of the sleeve to anchor the sleeve.

Figure 10:
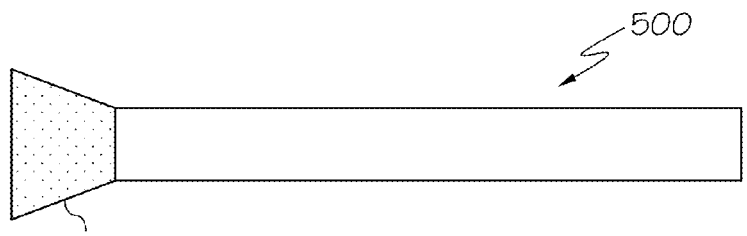
FIGS. 10-14 show schematics of various sleeves for the jejunum.
Figure 11:
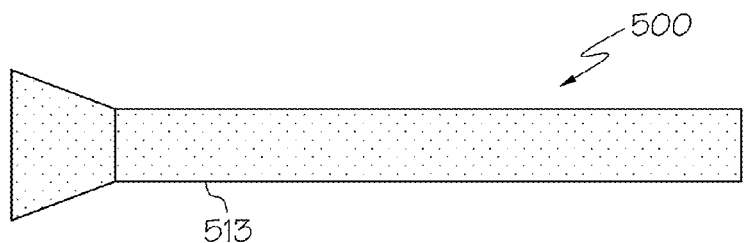
Figure 12:
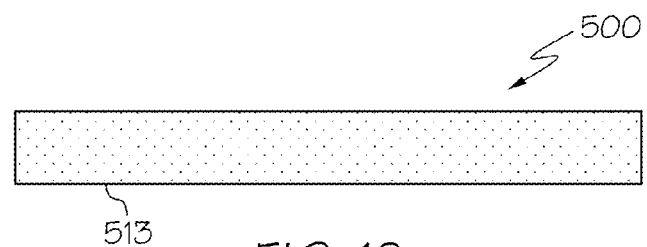
Figure 13:
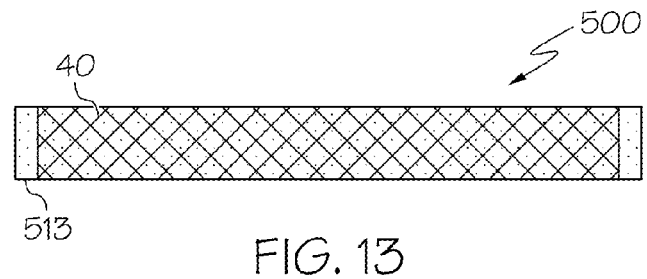
Figure 14:
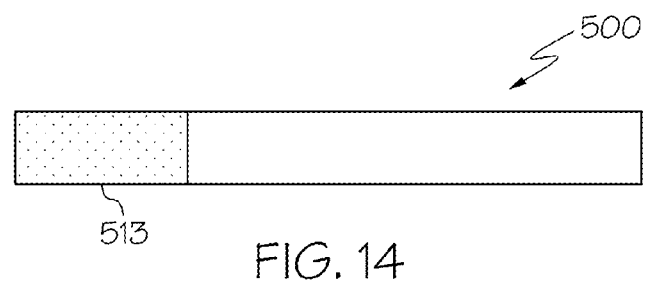

A number of embodiments for use in the jejunem are shown in FIGS. 10-14. FIG. 10 shows a jejunal liner in the form of sleeve 500 with adhesive micropattern 513 on the outer surface at one end. FIG. 11 shows another such sleeve 500 with adhesive micropattern 513 over the entirety of the outer surface. The sleeves of FIGS. 10 and 11 include an enlarged anchor portion at one end. FIG. 12 shows a sleeve 500 with adhesive micropattern 513 over the entire outer surface. The sleeve does not have an enlarged anchor portion. FIG. 13 shows a sleeve similar to that shown in FIG. 12, further comprising a stent 40. FIG. 14 shows a sleeve with a micropattern over only a portion of the sleeve.

These devices may also be used in the esophagus.

The sleeve may be adhered to the small intestine with a balloon. It may, optionally, be located distally of the papilla of Vaters.

The present disclosure is also directed to adjustable gastric bands provided with micropatterns on the outer surface to prevent migration. To that end, the band may be provided on the outer surface with any of the anti-migration patterns disclosed herein. As discussed above, these patterns have adhesive properties. The inner surface of the band may be provided with anti-adhesive micro-patterns which are used to prevent bacterial and biofilm adhesion. Thus, the superhydrophobic surface disclosed herein may be provided on an interior surface of the band. More details about gastric bands may be found at least in U.S. Pat. No. 6,755,869 (Geitz).

Antiadhesive micropatterns may also be provided inside a stent, inside a jejunal liner, outside a gastric balloon, or outside any device inserted in the stomach to treat obesity. Antiadhesive micropatterns may also be added to a tacky implant material such as SIBS (poly(styrene-block-isobutylene-block-styrene)), SIBS-PU ((poly(styrene-block-isobutylene-block-styrene)-polyurethane), or silicone to reduce tackiness and prevent adhesion.

Additionally, an adhesive micro-pattern may be applied to a device to maintain its location within an organ or subcutaneous location such as a port described in U.S. Pat. App. Pub. No. 2009/0182303 A1 (Walak et al.) for the treatment of obesity. An illustration of a port is shown in FIG. 15 of U.S. Pat. App. Pub. No. 2009/0182303 A1 (Walak et al.). The micro-pattern could be placed on the entire device or to elements of the device such as leads to ensure contact or delivery of a drug to the opposing tissue.

Additionally, an adhesive micro-pattern could be applied to a pacer, therapeutic agent release device, or obesity filler to maintain a position within the stomach or to join elements to form a filler of the stomach cavity so that the patient feels full.

The present disclosure is also directed to methods of making any of the medical devices disclosed herein as well as methods of using such devices in the body. Typically, the device will be delivered via catheter to a desired region of the body and deployed. Catheters are well known in the art and described in U.S. Pat. No. 6,071,273 (Euteneuer et al.), U.S. Pat. No. 6,733,487 (Keith et al.) and U.S. Pat. No. 6,254,609 (Vrba et al.).

A description of some embodiments of the present disclosure is contained in the following numbered statements:

Statement 1. A method for reducing mucus accumulation in an airway comprising:

disposing an implantable device within an airway, wherein the implantable device has a first end, a second end, and an inner surface defining a lumen extending from the first end to the second end;

wherein at least a portion of the inner surface has a hydrophobic polymer coating thereon, wherein a polymer coating surface has dynamic water contact angles of 145 degrees or greater; and wherein the implantable device is constructed and arranged to maintain patency of the airway;

wherein accumulation of mucus is reduced as compared to a similar implantable device without the hydrophobic portion of the inner surface.

Statement 2. The method of statement 1 wherein the implantable device comprises a stent.

Statement 3. The method of statement 1 or statement 2 wherein the hydrophobic coating comprises a superhydrophobic microstructure formed on the polymer coating surface.

Statement 4. The method of any one of statements 1-3 wherein disposing the implantable device within the airway comprises disposing the implantable device within a pulmonary airway.

Statement 5. The method of statement 4 wherein the pulmonary airway is selected from the group consisting of a main bronchus and a trachea.

Statement 6. An implantable medical device comprising:
an airway stent having a first end, a second end, and an inner surface defining a lumen extending from the first end to the second end;
a coating disposed over at least a portion of the inner surface, wherein a coating surface is hydrophobic and has dynamic water contact angles of 145 degrees or greater.

Statement 7. The implantable medical device of statement 6 wherein the implantable medical device has reduced adhesion with aqueous material and mucus material as compared to a similar stent without the coating.

Statement 8. The implantable medical device of statement 6 or statement 7 wherein the airway stent is structured and arranged to maintain the patency of an airway.

Statement 9. The implantable medical device of any one of statements 6-8 wherein the hydrophobic coating surface has dynamic water contact angles of 150 degrees or greater.

Statement 10. The implantable medical device of any one of claims 1-9 wherein the hydrophobic coating surface is near at least one of the first end and the second end.

Statement 11. The implantable medical device of any one of statements 6-10 wherein the hydrophobic coating surface extends from the first end to the second end.

Statement 12. A method for promoting transport of mucus in an airway comprising:
disposing an implantable medical device of any one of statements 6-11 in an airway.

Statement 13. A method for reducing inflammation at an implantation site comprising:
disposing an implantable medical device of any one of statements 6-11 at an implantation site in an airway.

Statement 14. A method for making an implantable device having a superhydrophobic surface comprising:
providing an airway stent having a first end, a second end, and an inner surface defining a lumen extending from the first end to the second end;
disposing on the airway stent a surface that is hydrophobic and has dynamic water contact angles of 145 degrees or greater.

Statement 15. The method of claim 14 wherein disposing a hydrophobic surface on the airway stent comprises:
disposing a polymer coating on at least the inner surface of the airway stent and forming a hydrophobic microstructure on the coating by one or more techniques selected from the group consisting of laser ablation, photolithography-based microfabrication, solidification of melted alkylketene dimer, microwave plasma enhanced chemical vapor deposition of trimethoxylmethoxysilane, phase separation, and domain selective oxygen plasma treatment; or
roughening an outer surface of a mandrel, placing an airway stent on the mandrel, applying a polymeric material to the airway stent and mandrel, and curing the polymeric material to form the hydrophobic surface in the form of an airway stent coating.

Statement 16. An implantable medical device having a surface, at least a portion of the surface being superhydrophobic.

Statement 17. The implantable medical device of statement 16 wherein a portion of the surface has a micropattern which provides enhanced adhesion to tissue as compared with other portions of the surface.

Statement 18. The implantable device of any of statements 16-17 wherein the device is tubular.

Statement 19. The implantable device of statement 18 wherein the device comprises a stent and the superhydrophobic surface is a surface of the stent.

Statement 20. The implantable device of statement 19 wherein the superhydrophobic surface is in the form of a polymeric coating.

Statement 21. The implantable device of statement 19 wherein the stent is made of a polymer.

Statement 22. The implantable device of any of statements 16-21 wherein the superhydrophobic surface is in an inner surface of the device and defines a lumen extending through the device.

Statement 23. The implantable device of any of statements 17-22 wherein the portion of the surface having a micropattern which provides enhanced adhesion is located at one end of the device.

Statement 24. The implantable device of any of statements 17-23 wherein the portion of the surface having a micropattern which provides enhanced adhesion is located at both ends of the device.

Statement 25. The implantable device of any of statements 17-24 in the form of an airway stent.

Statement 26. The implantable device of any of statements 17-24 in the form of an esophageal stent.

Statement 27. The implantable device of any of statements 17-26 wherein the superhydrophobic surface extends over the entirety of the inner surface of the device.

Statement 28. The implantable device of any of statements 17-26 wherein the superhydrophobic surface extends over only one end of the inner surface of the device.

Statement 29. The implantable device of any of statements 17-26 wherein the superhydrophobic surface extends over only a first end and a second end of the inner surface of the device, the remainder of the inner surface not having a superhydrophobic surface.

Statement 30. The implantable device of any of statements 17-29 wherein an outer surface of the device is provided at one end with a region having a micropattern which provides enhanced adhesion.

Statement 31. The implantable device of any of statements 17-29 wherein an outer surface of the device is provided at both ends with a region having a micropattern which provides enhanced adhesion.

Statement 32. The implantable device of any of statements 31 wherein an outer surface of the device is with a superhydrophobic region between the ends.

Statement 33. The implantable device of any of statements 17-24 and 27-33 in the form of a biliary stent.

Statement 34. The implantable device of any of statements 17-24 and 27-33 in the form of a pancreatic stent.

Statement 35. The implantable device of any of statements 17-34 wherein a portion of a surface of the device has a pattern of microprotrusions which extend parallel to one another.

Statement 36. The implantable device of any of statements 17-24, 27-33 and 35 in the form of a hemostasis clip.

Statement 37. The implantable device of any of statements 17-36 where the superhydrophobic region is characterized as having contact angles of at least 145 degrees.

The above disclosure is intended to be illustrative and not exhaustive. This description will suggest many variations and alternatives to a person of ordinary skill in this art. The various elements shown in the individual figures and described above can be combined or modified for combination as desired. All these alternatives and variations are intended to be included within the scope of the claims where the term "comprising" means "including, but not limited to".

Further, the particular features presented in the dependent claims can be combined with each other in other manners within the scope of the present disclosure such that the present disclosure should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

Those skilled in the art can recognize other equivalents to the specific embodiments described herein which equivalents are intended to be encompassed by the claims attached hereto.

What is claimed is:

1. An implantable medical device comprising:
a stent having a first end, a second end, an outer surface, and an inner surface defining a lumen extending from the first end to the second end; and
a coating disposed over at least a portion of the stent, wherein the coating includes a superhydrophobic micropattern on the inner surface which is hydrophobic and has dynamic water contact angles of 145 degrees or greater, and wherein the coating includes an anti-migration micropattern on the outer surface, the anti-migration micropattern including holes extending through the coating, the holes arranged between pillars of the anti-migration micropattern.

2. The implantable medical device of claim 1 wherein the implantable medical device has reduced adhesion with aqueous material and mucus material as compared to a similar stent without the coating.

3. The implantable medical device of claim 1 wherein the stent is structured and arranged to maintain the patency of a lumen.

4. The implantable medical device of claim 1 wherein the coating on the inner surface has dynamic water contact angles of 150 degrees or greater.

5. The implantable medical device of claim 1 wherein the superhydrophobic micropattern is adjacent at least one of the first end and the second end.

6. The implantable medical device of claim 1 wherein the superhydrophobic micropattern extends from the first end to the second end.

7. An implantable medical device comprising:
an stent having a first end, a second end, and an inner surface defining a lumen extending from the first end to the second end;
an anti-migration micropattern disposed on an outer surface of the stent, the anti-migration micropattern including holes extending through the coating, the holes arranged between pillars of the anti-migration micropattern; and
a hydrophobic polymer coating disposed on the inner surface, wherein a radially inwardly facing surface of the hydrophobic polymer coating has dynamic water contact angles of 145 degrees or greater.

8. The implantable medical device of claim 7, wherein the hydrophobic polymer coating includes a superhydrophobic microstructure formed on the radially inwardly facing surface.

9. The implantable medical device of claim 7, wherein the hydrophobic polymer coating includes a micropattern.

10. The implantable medical device of claim 7, wherein the radially inwardly facing surface of the hydrophobic polymer coating has dynamic water contact angles of greater than 160 degrees.

11. The implantable medical device of claim 7, wherein the radially inwardly facing surface of the hydrophobic polymer coating has dynamic water contact angles of greater than 170 degrees.

12. The implantable medical device of claim 7, wherein the anti-migration micropattern includes at least one region of the stent having openings devoid of any coating on the inner surface and an outer surface.

13. The implantable medical device of claim 12, wherein the anti-migration micropattern includes first and second regions of the stent having openings devoid of any coating, the first and second regions disposed at the first and second ends of the stent, respectively, wherein a middle region between the first and second regions has an outer surface with a superhydrophobic coating.

14. The implantable medical device of claim 7, wherein the polymer coating and the stent are formed as an integral construction, wherein the polymer coating defines a micropattern directly incorporated into a structure of the stent.

15. An implantable medical device comprising:
an airway stent having a first end, a second end, an outer surface, and an inner surface defining a lumen extending from the first end to the second end; and
a coating disposed over at least a portion of at least one of the inner and outer surfaces, wherein a coating surface of the coating has a micropattern and is hydrophobic with dynamic water contact angles of 145 degrees or greater, wherein the micropattern includes pillars and holes between the pillars extending through the coating.

16. The implantable medical device of claim 15, wherein the holes are between 0.3 microns and 20 microns across.

17. The implantable medical device of claim 16, wherein the holes are between 1 micron and 10 microns across.

18. The implantable medical device of claim 15, wherein the coating is disposed over at least a portion of the inner surface of the stent.

19. The implantable medical device of claim 18, wherein the coating is disposed over at least a portion of both the inner and outer surfaces of the stent.

20. The implantable medical device of claim 18, wherein at least a portion of the outer surface of the stent includes an anti-migration micropattern.

* * * * *